United States Patent
Osei-Gyimah et al.

[11] Patent Number: 5,508,417
[45] Date of Patent: Apr. 16, 1996

[54] BROAD-SPECTRUM ISOTHIAZOLE ANTIMICROBIAL AGENTS

[75] Inventors: Peter Osei-Gyimah, Horsham; Barry C. Lange, Lansdale, both of Pa.

[73] Assignee: Rohm and Haas Company, Philadelphia, Pa.

[21] Appl. No.: 200,254

[22] Filed: Feb. 23, 1994

[51] Int. Cl.$^6$ .............. C07D 275/02; C07D 409/12; A61K 31/425
[52] U.S. Cl. .............................. 548/213; 548/113
[58] Field of Search .................. 548/213, 113; 517/439, 444, 92

[56] References Cited

U.S. PATENT DOCUMENTS 3,957,808  5/1976  Miller et al. ............... 260/302

FOREIGN PATENT DOCUMENTS 3202289  8/1983  Germany .

Primary Examiner—David B. Springer
Attorney, Agent, or Firm—Michael B. Fein

[57] ABSTRACT

This invention relates to antimicrobial compounds of formula I, II, or III

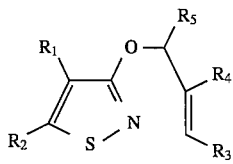

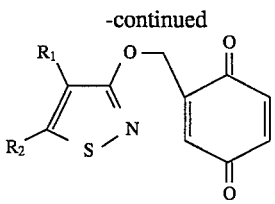

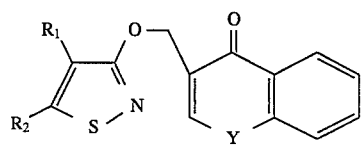

wherein $R_1$ and $R_2$ are independently selected from hydrogen, halogen, or $(C_1-C_4)$alkyl;

$R_1$ and $R_2$ may be taken together with the carbons to which they are attached to form a 5 to 7-membered carbocyclic ring and the ring may be aromatic;

$R_3$ is hydrogen, $(C_1-C_8)$alkyl, $(C_2-C_8)$alkenyl, $(C_5-C_8)$alkynyl, $(C_5-C_7)$cycloalkyl or cycloalkenyl, phenyl or substituted phenyl, $(C_7-C_{10})$aralkyl or substituted $(C_7-C_{10})$aralkyl, or a 5 to 8-membered heteroaryl having one or more heteroatoms selected from the group consisting of oxygen, sulfur and nitrogen;

$R_4$ is an electron-withdrawing group selected from CN, $NO_2$, $P(O)(OR_7)_2$, $P(S)(OR_7)_2$, $COOR_6$, $COR_6$, $CONHR_6$, $SOR_6$, $SO_2R_6$, where $R_6$ is hydrogen, $(C_1-C_8)$alkyl, phenyl or substituted phenyl, $(C_7-C_{10})$aralkyl or substituted $(C_7-C_{10})$aralkyl, $(C_5-C_7)$cycloalkyl, or a 5 to 8-membered heteroaryl having one or more heteroatoms selected from the group consisting of oxygen, sulfur and nitrogen and where $R_7$ is $(C_1-C_4)$alkyl or phenyl;

$R_3$ and $R_4$ may be joined to form a $(C_5-C_7)$cycloalkenone optionally containing a heteroatom selected from the group consisting of oxygen, sulfur and nitrogen;

$R_5$ is hydrogen or $(C_1$ to $C_4)$alkyl; and

Y is oxygen, sulfur, sulfoxide, sulfone, or nitrogen substituted with $(C_1-C_4)$alkyl, $(C_3-C_5)$cycloalkyl, or phenyl.

3 Claims, No Drawings

BROAD-SPECTRUM ISOTHIAZOLE ANTIMICROBIAL AGENTS

BACKGROUND OF THE INVENTION

1. Field of the Invention

This invention relates to novel microbicide compounds.

2. Description of the Prior Art

U.S. Pat. No. 3,957,808 assigned to Rohm and Haas Company discloses 3-alkoxyisothiazoles, including Compound A, and their compositions containing them to exhibit useful microbicidal properties.

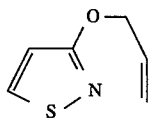   A

SUMMARY OF THE INVENTION

It is an object of the present invention to provide microbicide compounds which have fungicidal, bactericidal and/or algaecidal activity and function to kill or inhibit the growth of microbial organisms present in various loci.

This and other objects which will become apparent from the following disclosure are achieved by the present invention which in one aspect comprises compounds of the formulae I, II, and III

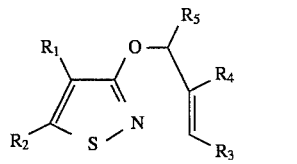   I

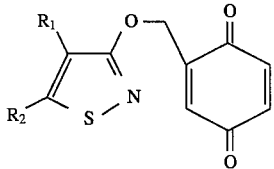   II

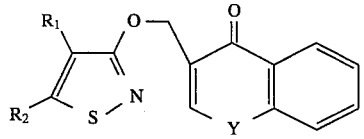   III wherein $R_1$ and $R_2$ are independently selected from hydrogen, halogen, or $(C_1-C_4)$alkyl;

$R_1$ and $R_2$ may be taken together with the carbons to which they are attached to form a 5 to 7-membered carbocyclic ring and the ring may be aromatic;

$R_3$ is hydrogen, $(C_1-C_8)$alkyl, $(C_2-C_8)$alkenyl, $(C_2-C_8)$alkynyl, $(C_5-C_7)$cycloalkyl or cycloalkenyl, phenyl or substituted phenyl, $(C_7-C_{10})$aralkyl or substituted $(C_7-C_{10})$aralkyl, or a 5 to 8-membered heteroaryl having one or more heteroatoms selected from the group consisting of oxygen, sulfur and nitrogen;

$R_4$ is an electron-withdrawing group selected from CN, $NO_2$, $P(O)(OR_7)_2$, $P(S)(OR_7)_2$, $COOR_6$, $COR_6$, $CONHR_6$, $SOR_6$, $SO_2R_6$, where $R_6$ is hydrogen, $(C_1-C_8)$alkyl, phenyl or substituted phenyl, $(C_7-C_{10})$aralkyl or substituted $(C_7-C_{10})$aralkyl, $(C_5-C_7)$cycloalkyl, or a 5 to 8-membered heteroaryl having one or more heteroatoms selected from the group consisting of oxygen, sulfur and nitrogen and where $R_7$ is $(C_1-C_4)$alkyl or phenyl;

$R_3$ and $R_4$ may be joined to form a $(C_5-C_7)$cycloalkenone optionally containing a heteroatom selected from the group consisting of oxygen, sulfur and nitrogen;

$R_5$ is hydrogen or $(C_1$ to $C_4)$alkyl; and

Y is oxygen, sulfur, sulfoxide, sulfone, or nitrogen substituted with $(C_1-C_4)$alkyl, $(C_3-C_5)$cycloalkyl, or phenyl.

The invention also relates to the use of the novel compounds in, at, or on various loci in amounts sufficient to control or inhibit the growth of microbial organisms.

DETAILED DESCRIPTION OF THE INVENTION AND THE PREFERRED EMBODIMENTS

By substituted phenyl is meant a phenyl group having one or more of its hydrogens replaced with another substituent group. Examples of suitable substituent groups include $(C_1-C_3)$alkyl, $(C_1-C_3)$alkoxy, hydroxy, nitro, halo, cyano, (and $C_1-C_3$)alkylthio.

By substituted $(C_7-C_{10})$aralkyl is meant a $(C_7-C_{10})$aralkyl group having one or more of its hydrogens replaced with another substituent group. Examples of suitable substituent groups include $(C_1-C_3)$alkyl, $(C_1-C_3)$alkoxy, hydroxy, nitro, halo, cyano, (and $C_1-C_3$)alkylthio.

By 5 to 8-membered heteroaryl is meant a 5 to 8-membered aromatic ring having at least one heteroatom selected from the group consisting of oxygen, sulfur and nitrogen. Examples of suitable heteroaryls include thienyl, furanyl, pyridinyl, triazolyl, and the like.

As used herein, "microbicides" includes fungicides, bactericides and algaecides and microbicidal activity is intended to include both the elimination of and inhibition or prevention of growth of microbial organisms such as fungi, bacteria, and algae.

The alkenyl isothiazole ethers of this invention may be prepared by known alkylation methods. For example, an appropriate 3-hydroxyisothiazole can be treated with an inorganic base, such as potassium or sodium carbonate or sodium hydride in a solvent such as acetonitrile, dimethyl formamide or tetrahydrofuran to generate the salt which is then allowed to react with the appropriately substituted alkylating agent.

The alkylation reaction takes place over a broad range of temperature of 25°–100° C. and proceeds within 1–24 hours. Equimolar quantities of the 3-hydroxyisothiazole, base, and the alkylating agent are preferably used in this reaction.

The 3-hydroxyisothiazoles useful in this invention are of formula IV

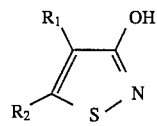   IV where $R_1$ and $R_2$ are independently selected from hydrogen, halogen, or $(C_1-C_4)$alkyl; $R_1$ and $R_2$ may be taken together with the carbons to which they are attached to form a 5 to 7-membered carbocyclic ring and the ring may be aromatic.

The alkylating agents useful in this invention are of formulae V, VI, and VII

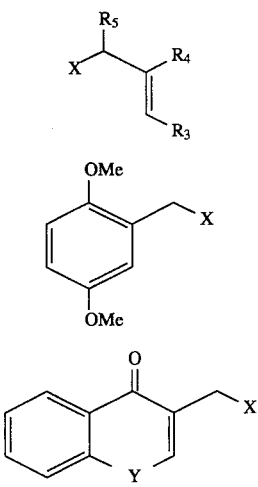

where

X is a halogen and is preferably bromine, chlorine or iodine;

$R_3$ is hydrogen, $(C_1-C_8)$alkyl, $(C_2-C_8)$alkenyl, $(C_2-C_8)$alkynyl, $(C_5-C_7)$cycloalkyl or cycloalkenyl, phenyl or substituted phenyl, $(C_7-C_{10})$aralkyl or substituted $(C_7-C_{10})$aralkyl, or a 5 to 8-membered heteroaryl having one or more heteroatoms selected from the group consisting of oxygen, sulfur and nitrogen;

$R_4$ is an electron-withdrawing group selected from CN, $NO_2$, $P(O)(OR_7)_2$, $P(S)(OR_7)_2$, $COOR_6$, $COR_6$, $CONHR_6$, $SOR_6$, $SO_2R_6$, where $R_6$ is hydrogen, $(C_1-C_8)$alkyl, phenyl or substituted phenyl, $(C_7-C_{10})$aralkyl or substituted $(C_7-C_{10})$aralkyl, $(C_5-C_7)$cycloalkyl, or a 5 to 8-membered heteroaryl having one or more heteroatoms selected from the group consisting of oxygen, sulfur and nitrogen and where $R_7$ is $(C_1-C_4)$alkyl or phenyl;

$R_3$ and $R_4$ may be joined to form a $(C_5-C_7)$cycloalkenone optionally containing a heteroatom selected from the group consisting of oxygen, sulfur and nitrogen;

$R_5$ is hydrogen or $(C_1$ to $C_4)$alkyl; and

Y is oxygen, sulfur, sulfoxide, sulfone, or nitrogen substituted with $(C_1-C_4)$alkyl, $(C_3-C_5)$cycloalkyl, or phenyl.

The compounds of formula I can be prepared by reacting a salt of a 3-hydroxyisothiazole of formula IV with an alkylating agent of formula V. The compounds of formula II are similarly prepared by reacting a salt of 3-hydroxyisothiazole with an alkylating agent of formula VI, followed by oxidation according to the known procedure using ceric ammonium nitrate in water-acetonitrile solution. This oxidation reaction occurs over 1–60 minutes at 0°–50° C. The compounds of formula III can be prepared by reacting a salt of a 3-hydroxyisothiazole with an alkylating agent of formula VII.

The substituted alkylating agents suitable for the alkylation reactions to give compounds of formulae I, II, or III are generally known and are available commercially or can be prepared by methods known in the art. Examples of suitable alkylating agents include methyl 2-bromomethyl acrylate, 2-bromomethyl acrylic add, ethyl 2-bromomethyl-2-butenoate, ethyl 3-phenyl-2-bromomethyl acrylate, 2-bromomethyl-3-phenyl acrylonitrile, ethyl 3-phenyl-2-bromomethyl acrylate, α-(bromomethyl)benzalacetone, 3-chloro-2-(phenylsulfinyl)-1-propene, 3-chloro-2-(phenylsulfonyl)-1-propene, N-substituted-2-bromomethylacrylamides, 3-bromo-2-(dimethylphosphonyl)-1-propene, 3-bromo-2-nitro-1-propene, 2-chloromethyl-2-cyclopentenone, 2,5-dimethoxybenzyl chloride, and 3-chloromethyl chromone.

The following are a few of the preferred compounds of the invention.

1. Methyl 2-(isothiazoloxy-3-yl-methyl)acrylate
2. Methyl 2-(5-chloroisothiazoloxy-3-yl-methyl)acrylate
3. Ethyl 3-methyl-2-(5-chloroisothiazoloxy-3-yl-methyl)acrylate
4. 2-(5-Chloroisothiazoloxy-3-yl-methyl)-3-phenylacrylonitrile
5. α-(5-Chloroisothiazoloxy-3-yl-methyl)benzalacetone
6. 3-(5-Chloroisothiazoloxy-3-yl-methyl)-2-phenylsulfinyl-1-propene
7. 3-(5-Chloroisothiazoloxy-3-yl-methyl)-2-phenylsulfonyl-1-butene
8. 1-(5-Chloroisothiazoloxy-3-yl-methyl)-2-phenylsulfonyl-2-butene
9. N-Benzyl 2-(5-chloroisothiazoloxy-3-yl-methyl)acrylamide
10. 2-(5-Chloroisothiazoloxy-3-yl-methyl)acrylic acid
11. α-(4,5-Trimethyleneisothiazoloxy-3-yl-methyl)benzalacetone
12. N-Isopropyl 2-(5-chloroisothiazoloxy-3-yl-methyl)acrylamide
13. 3-(5-Chloroisothiazoloxy-3-yl-methyl)chromone
14. 2-(5-Chloroisothiazoloxy-3-yl-methyl)-1,4-benzoquinone
15. 2-(Isothiazoloxy-3-yl-methyl)-1,4-benzoquinone The compounds of the invention can be used to inhibit the growth of microbial organisms by introducing a microbicidally effective amount of one or more of said compounds onto, into, or at a locus subject to microbial attack. Loci such as wood, paint, adhesive, caulk, mastic, latex, pulp/paper slurries, textile, leather, plastics, cardboard, lubricants, cosmetics, industrial cooling water, metal working fluid, pigment slurries, photographic processing fluids, and fuels can be protected.

The amount of compound suitable to inhibit the growth of microbial organisms is from about 5 to 300 ppm based on weight of said locus. Generally, the microbicide is applied in a carrier such as water, solvent, or the like.

It is known in the art that the performance of microbicides may be enhanced by combination with one or more other microbicides. Thus, other known microbicides may be combined advantageously with the compounds of this invention.

The following examples set forth a few embodiments of the invention but are not to be construed as limitations thereof. All parts and percentages are by weight unless otherwise indicated.

EXAMPLES

Example 1: Preparation of Methyl 2-(isothiazoloxy-3-yl-methyl) acrylate (Compound 1)

A mixture of 3-hydroxyisothiazole (1.5 g, 0.015 mole) and powdered, anhydrous $K_2CO_3$ (2.2 g, 0.016 mol) in 25 ml of dry acetonitrile was stirred at room temperature and under $N_2$ flow for 30 minutes. A solution of methyl 2-bromomethyl acrylate (2.65 g, 0.015 mole) in 5 ml of dry acetonitrile was added dropwise. The mixture was stirred for 24 hours at room temperature and then poured into water and extracted with ethyl acetate. The ethyl acetate extract was washed with water, dried ($MgSO_4$) and concentrated. The residual oil was purified by column chromatography on silica gel, using Et$_2$O/hexane (1/1) as eluant. Compound 1 was obtained as a white solid; 0.8 g; mp 46°–48° C.; IR (KBr) 1725 cm$^{-1}$; NMR (CDCl$_3$) δ 8.5 (d, 1H); 6.65 (d, 1H); 6.45 (s, 1H); 6.0 (s, 1H); 5.15 (s, 2H); 3.82 (3, 3H)

Example 2: Preparation of 3-(5-Chloroisothiazoloxy-3-yl)-2-phenylsulfonyl-1-butene and 1-(5-Chloroisothiazoloxy-3-yl-methyl)-2-phenylsulfonyl-2-butene (Compounds 7 and 8)

A mixture of 5-chloro-3-hydroxyisothiazole (1.5 g, 0.011 mole) and powdered, anhydrous K$_2$CO$_3$ (1.66 g, 0.012 mole) in dry acetonitrile (25 ml) was stirred at room temperature under N$_2$ flow for 30 minutes. A solution of 1-bromo-2-phenylsulfonyl-2-butene (3.03 g, 0.011 mol) in 10 ml of acetonitrile was added dropwise. The mixture was stirred at room temperature for 24 hours and then poured into water and extracted with methylene chloride. The methylene chloride extract was successively washed with water and brine and then dried (MgSO$_4$) and concentrated. The residual brown oil which consisted of a mixture of compounds 7 and 8 was column-chromatographed on silica gel to separate the products, using diethyl ether/hexane (1/1) as eluant. Compound 7 which eluted first was obtained as a white solid; 0.25 g; mp 50°–53° C.; NMR (CDCl$_3$) δ 7.8–7.9 (m, 2H); 7.45–7.7 (m, 3H); 6.5 (s, 1H); 6.1–6.2 (m, 2H); 5.6– 5.7 (m, 1H); 1.55–1.65 (d, 3H).

Compound 8 was obtained as a yellowish white solid; 1.4 g; mp 81 –83° C.; NMR (CDCl$_3$) δ 7.82–7.90 (m, 2H); 7.5–7.7 (m, 3H); 7.3–7.4 (m,1H); 6.1 (s, 1H); 4.62 (s, 2H); 2.02–2.1 (d, 2H).

Example 3: Preparation of 2-(5-Chloroisothiazoloxy-3-yl-methyl)acrylic acid (Compound 10)

To a solution of KOH (1.2 g, 0.02 mole) in 20 ml of ethanol/water (3/1) was added 5 -chloro-3-hydroxyisothiazole (2.7 g, 0.02 mole) and stirred to dissolve. The solution obtained was added dropwise to a stirred solution of 2-bromomethyl acrylic acid (3.3 g, 0.02 mole) in aqueous KOH (1.2 g, 0.02 mole) in 10 ml of water. The mixture was stirred for 24 hours at room temperature. The mixture was extracted with ethyl ether which was discarded. The aqueous portion was acidified with 2N HCl solution and extracted with ethyl acetate. The ethyl acetate extract was washed with water, dried (MgSO$_4$) and concentrated. The residual yellowish solid was suspended in diethyl ether/acetone mixture (1/1), chilled and removed by filtration. Compound 10 was obtained as a pale yellow solid; 0.85 g; m p 163°–167° C.; NMR (DMSO-d$_6$) δ11.4–11.7 (br., 1H); 6.3 (s, 1H); 6.15 (s, 1H); 5.87 (s, 1H); 4.25 (s, 1H).

Example 4: Preparation of α-(4,5-Trimethyleneisothiazoloxy-3-yl-methyl) benzalacetone (Compound 11)

A mixture of 4,5-trimethylene-3-hydroxyisothiazole (1.23 g, 0.008 mole) and anhydrous K$_2$CO$_3$ (1.25 g, 0.009 mole) in 20 ml of acetonitrile was stirred at room temperature for 30 minutes. A solution of α-bromobenzalacetone (1.85 g, 0.008 mole) in 15 ml of acetonitrile was added dropwise. The mixture was stirred at room temperature for 24 hours and then poured into water and extracted with ethyl acetate. The ethyl acetate extract was washed with water, dried (MgSO$_4$) and concentrated. The residual oil was purified by column chromatography on silica gel, using diethyl ether/ hexane (7/3) as eluant. Compound 11 was obtained as a light yellow off; 0.93 g; IR (neat) 1675 cm$^{-1}$; NMR (CDCl$_3$) δ 7.85 (s, 1H); 7.35–7.55 (m, 5H); 5.25 (s, 2H); 2.9–3.0 (m, 2H); 2.55–2.62 (m, 4H); 2.5 (s, 3H).

Example 5: Preparation of 2-(5-Chloroisothiazoloxy-3-yl-methyl)-1,4-benzoquinone (Compound 14)

A solution of 5-chloro-3-hydroxyisothiazole (4.0 g, 0.03 mole) in 15 ml of dimethyl formamide was added dropwise to a stirred suspension of 60% NaH in oil (1.4 g, 0.035 mole) in 25 ml of dimethyl formamide at 0° C. under N$_2$. After 15 minutes, a solution of 2,5-dimethoxybenzyl chloride (5.6 g, 0.03 mole) in 10 ml of dimethyl formamide was added dropwise and the mixture was stirred at room temperature for 24 hours. The dark reaction mixture was poured into water and extracted with diethyl ether. The diethyl ether extract was washed with water, dried (MgSO$_4$), and concentrated. The residual white solid was purified by column chromatography on silica gel, using diethyl ether/hexane (1/1) as eluant. 5-Chloro-3-(2,5-dimethoxybenzyloxy-)isothiazole was obtained as a white solid; 4.7 g; mp 52°–55° C.

Ceric ammonium nitrate (6.4 g, 0.012 mole) in 25 ml of water was added dropwise to a stirred solution of 5-chloro-3-(2,5-dimethoxybenzyloxy)isothiazole (1.5 g, 0.053 mole) in 25 ml of acetonitrile. After stirring at room temperature for 30 minutes, the mixture was diluted with water and extracted with chloroform. The chloroform extract was washed with water, brine and dried (MgSO$_4$). The solvent was removed by evaporation to give a brown, solid residue which was purified by column chromatography on silica gel, using hexane/diethyl ether (3/2) as eluant. Compound 14 was obtained as a reddish-brown solid; 0.8 g; mp 119°–122° C.; IR (KBr) 1660 cm$^{-1}$; NMR (CDCl$_3$) δ 6.8 (s, 2H); 6.65 (s, 1H); 5.3 (s, 1H).

Example 6: Biological Activity

The alkenyl isothiazole ethers of this invention demonstrated antimicrobial activity against bacteria and fungi. A stock solution of the test compound was made in dimethyl sulfoxide at 13,000 ppm and then diluted 26-fold to give a starting concentration of 500 ppm. The antimicrobial activity was evaluated by a two-fold serial dilution of the starting concentration of 500 ppm, using Trypticase Soy Broth medium at pH 7.0. The test organisms used to demonstrate antimicrobial activity are listed in Table 1. The minimum inhibitory concentration (MIC) of compounds 1–15 against the test organisms are shown in Table 2.

TABLE 1

| Microorganisms used in the Antimicrobial Test | |
|---|---|
| Name | Abbreviations Used |
| Bacteria | |
| Pseudomonas aeruginosa | Psae |
| Escherichia coli | Ecol |
| Staphlococcus aureus | Saur |
| Fungus | |
| Aspergillus niger | Anig |

TABLE 2

Antimicrobial Activity (MIC, ppm) of Compounds 1–15

| Comp. No. | Psae | Ecol | Saur | Anig |
|---|---|---|---|---|
| 1 | 32 | 32 | — | 32 |
| 2 | 32 | 2 | 4 | 1 |
| 3 | 125 | 8 | 8 | 4 |
| 4 | >500 | >500 | 500 | 500 |
| 5 | 16 | 4 | 2 | 1 |
| 6 | 125 | 125 | 125 | 32 |
| 7 | 32 | 32 | 32 | 32 |
| 8 | 64 | 32 | 32 | 64 |
| 9 | >500 | >500 | >500 | 32 |
| 10 | >500 | 125 | 64 | >500 |
| 11 | >500 | >500 | >500 | 500 |
| 12 | 500 | 500 | >500 | 64 |
| 13 | 32 | 8 | 8 | 16 |
| 14 | 64 | 16 | 64 | 8 |
| 15 | 32 | 64 | 32 | 16 |

Example 7-Comparative

Two compounds representative of U.S. Pat. No. 3,957,808 were prepared and identified as compounds A and B respectively and were compared to compounds 1 and 2 of the invention with respect to certain anti-microbial activity. These four compounds have the following formulae:

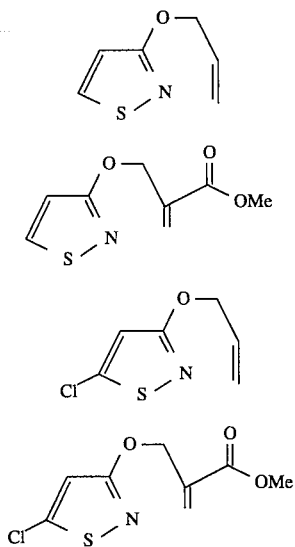

The antimicrobial activity of these compounds was determined as described in Example 6 with only one change. The organism Saur was replaced by *Rhodotorula rubra* (Rrub). Rrub is a pink yeast. These data are reported in Table 3.

TABLE 3

Comparative Antimicrobial Activity (MIC, ppm)

| Compound | Ecol | Psae | Anig | Rrub |
|---|---|---|---|---|
| A* | >500 | >500 | 500 | >500 |
| 1 | 32 | 32 | 32 | 32 |
| B* | 250 | 500 | 250 | 500 |
| 2 | <4 | 32 | 4 | 8 |

*= comparative

From these data, it can be seen that the compounds of the invention have unexpectedly greater antimicrobial activity than the analogs of the prior art.

Example 8

Melting points of the compounds of the invention were determined to be as follows

| Compound | Melting Point |
|---|---|
| 1 | 46–48° C. |
| 2 | 59–62° C. |
| 3 | Oil |
| 4 | 63–66° C. |
| 5 | 109–112° C. |
| 6 | Oil |
| 7 | 50–53° C. |
| 8 | 81–83° C. |
| 9 | 67–70° C. |
| 10 | 163–167° C. |
| 11 | Oil |
| 12 | 75–77° C. |
| 13 | 134–136° C. |
| 14 | 119–122° C. |
| 15 | 125–127° C. |

While this invention has been described in considerable detail, various modifications, alternates and improvements should become apparent to those skilled in the art without departing from the spirit and scope of the invention.

What is claimed is:

1. Antimicrobial compounds of formula I, II, or III

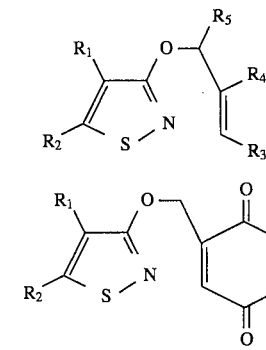

wherein $R_1$ and $R_2$ are independently selected from hydrogen, halogen, or $(C_1-C_4)$alkyl;

$R_1$ and $R_2$ may be taken together with the carbons to which they are attached to form a 5 to 7-membered carbocyclic ring and the ring may be aromatic;

$R_3$ is hydrogen, $(C_1-C_8)$alkyl, $(C_2-C_8)$alkenyl, $(C_2-C_8)$alkynyl, $(C_5-C_7)$cycloalkyl or cycloalkenyl, phenyl or phenyl substituted with a substituent selected from $(C_1-C_3)$alkyl, $(C_1-C_3)$alkoxy, hydroxy, nitro, halo, cyano, and $(C_1-C_3)$alkylthio, $(C_7-C_{10})$aralkyl or $(C_7-C_{10})$aralkyl substituted with a substituent selected from $(C_1-C_3)$alkyl, $(C_1-C_3)$alkoxy, hydroxy, nitro, halo, cyano, and $(C_1-C_3)$alkylthio, or a 5 to 8-membered heteroaryl having one or more heteroatoms selected from the group consisting of oxygen and sulfur;

$R_4$ is an electron-withdrawing group selected from CN, $NO_2$, $P(C))(OR_7)_2$, $P(S)(OR_7)_2$, $COOR_6$, $COR_6$, $CONHR_6$, $SOR_6$, $SO_2R_6$, where $R_6$ is hydrogen, $(C_1-C$ s)alkyl, phenyl or substituted phenyl, $(C_7-C_{10})$aralkyl or substituted $(C_7-C_{10})$aralkyl, $(C_5-C_7)$cycloalkyl, or a 5 to 8-membered heteroaryl having one or more heteroatoms selected from the group consisting of oxygen and sulfur; and where $R_7$ is $(C_1-C_4)$alkyl or phenyl;

$R_3$ and $R_4$ may be joined to form a $(C_5-C_7)$cycloalkenone optionally containing a heteroatom selected from the group consisting of oxygen and sulfur;

$R_5$ is hydrogen or $(C_1$ to $C_4)$alkyl; and

Y is oxygen, sulfur, sulfoxide, or sulfone substituted with $(C_1-C_4)$alkyl, $(C_3-C_5)$cycloalkyl, or phenyl.

2. Compounds selected from the group consisting of methyl 2-(isothiazoloxy-3-yl-methyl)acrylate;

methyl 2-(5-chloroisothiazoloxy-3-yl-methyl)acrylate;

ethyl 3-methyl-2-(5-chloroisothiazoloxy-3-yl-methyl)acrylate;

2-(5-chloroisothiazoloxy-3-yl-methyl)-3-phenylacrylonitrile;

α-(5-chloroisothiazoloxy-3-yl-methyl)benzalacetone;

3-(5-chloroisothiazoloxy-3-yl-methyl)-2-phenylsulfinyl-1-propene;

3-(5-chloroisothiazoloxy-3-yl-methyl)-2-phenylsulfonyl-1-butene;

1-(5-chloroisothiazoloxy-3-yl-methyl )2-phenylsulfonyl-2-butene;

N-benzyl 2-(5-chloroisothiazoloxy-3-yl-methyl)acrylamide;

2-(5-chloroisothiazoloxy-3-yl-methyl)acrylic acid;

α-(4,5-trimethyleneisothiazoloxy-3-yl-methyl)benzalacetone;

N-isopropyl 2-(5-chloroisothiazoloxy-3-yl-methyl)acrylamide;

3-(5-chloroisothiazoloxy-3-yl-methyl)chromone;

2-(5-chloroisothiazoloxy-3-yl-methyl)-1,4-benzoquinone; and 2-(isothiazoloxy-3-yl-methyl)-1,4-benzoquinone.

3. Method of inhibiting microbial growth in a locus comprising introducing in, at, or on said locus a sufficient amount of a compound according to claim 1 to control the growth of fungi, bacteria, or algae at said locus.

* * * * *